United States Patent [19]

Hoehn et al.

[11] 4,111,940
[45] Sep. 5, 1978

[54] 1,5,6,11-TETRAHYDRO[5,6]CYCLOHEPTA-[1,2,-b]PYRAZOLO[4,3-e]PYRIDINE DERIVATIVES

[75] Inventors: Hans Hoehn, Tegernheim, Fed. Rep. of Germany; Jack Bernstein, New Brunswick, N.J.; Berthold Richard Vogt, Yardley, Pa.

[73] Assignee: E. R. Squibb & Sons, Inc., Princeton, N.J.

[21] Appl. No.: 785,398

[22] Filed: Apr. 7, 1977

[51] Int. Cl.$^2$ .................................... C07D 471/04
[52] U.S. Cl. ........................... 260/293.6; 260/296 P; 424/267; 544/361
[58] Field of Search ........................ 260/293.6

Primary Examiner—Jose Tovar
Attorney, Agent, or Firm—Lawrence S. Levinson; Merle J. Smith; Stephen B. Davis

[57] ABSTRACT

Various 1,5,6,11-tetrahydrobenzo[5,6]cyclohepta[1,2-b]-pyrazolo[4,3-e]pyridine derivatives and their salts of the formulas

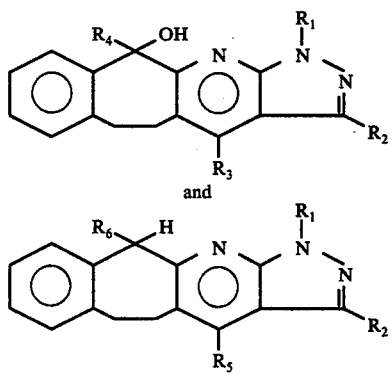

and wherein $R_1$ is lower alkyl, phenyl, or phenyl-lower alkyl; $R_2$ is hydrogen, lower alkyl or phenyl; $R_3$ is hydrogen, halogen, or lower alkoxy; $R_4$ is hydrogen,

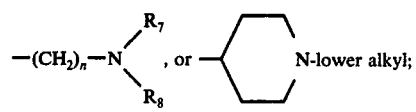

alkyl; $R_5$ is hydrogen or lower alkoxy; $R_6$ is hydrogen,

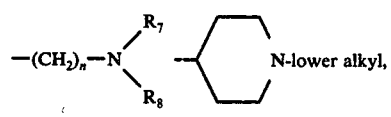

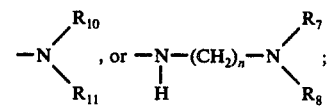

$n$ is an integer from 2 to 6; $R_7$ and $R_8$ are the same or different and each is lower alkyl or $R_7$ and $R_8$ taken together with the N-atom form a heterocyclic ring of the formula

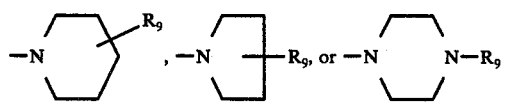

wherein $R_9$ is hydrogen or lower alkyl; $R_{10}$ and $R_{11}$ are the same or different and each is hydrogen or lower alkyl or $R_{10}$ and $R_{11}$ taken together with the N-atom form a heterocyclic ring of the formula

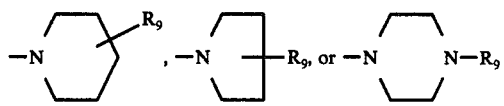

wherein $R_9$ is as defined above; are disclosed. These compounds possess useful antiinflammatory activity as well as psychotropic activity.

7 Claims, No Drawings

1,5,6,11-TETRAHYDRO[5,6]CYCLOHEPTA-[1,2,-B]PYRAZOLO[4,3-E]PYRIDINE DERIVATIVES

SUMMARY OF THE INVENTION

This invention relates to new 1,5,6,11-tetrahydrobenzo[5,6]cyclohepta[1,2-b]pyrazolo[4,3-e]pyridine derivatives and their salts of the formulas

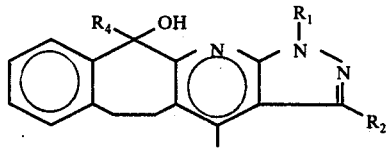
(I)

and

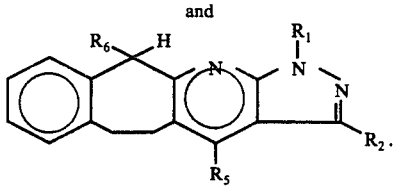
(II)

$R_1$ is hydrogen, lower alkyl, phenyl, or phenyl-lower alkyl.

$R_2$ is hydrogen, lower alkyl, or phenyl.

$R_3$ is hydrogen, halogen or lower alkoxy.

$R_4$ is hydrogen,

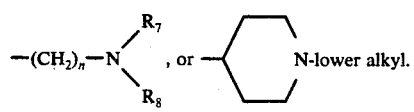

$R_5$ is hydrogen or lower alkoxy.

$R_6$ is hydrogen,

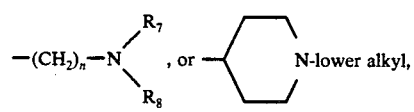

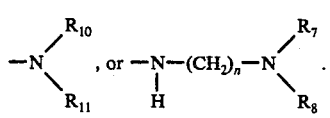

n is a integer from 2 to 6.

$R_7$ and $R_8$ are the same or different and each is lower akly or $R_7$ and $R_8$ taken together with the N-atom to which they are attached form a heterocyclic ring of the formula

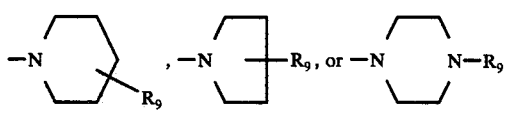

wherein $R_9$ is hydrogen or lower alkyl.

$R_{10}$ and $R_{11}$ are independently selected from hydrogen and lower alkyl or $R_{10}$ and $R_{11}$ taken together with the N-atom to which they are attached form a heterocyclic ring of the formula

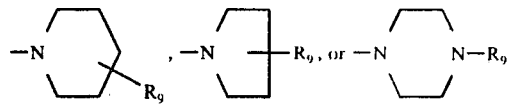

wherein $R_9$ is as defined above.

Preferred embodiments of this invention are the compounds of formula I and their pharmaceutically acceptable salts wherein:

$R_1$ is lower alkyl, especially ethyl.

$R_2$ is hydrogen.

$R_3$ is hydrogen, Cl, Br, or lower alkoxy, especially hydrogen, Cl, or methoxy.

$R_4$ is hydrogen,

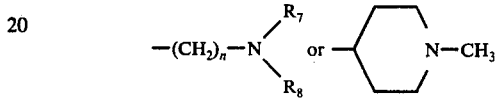

wherein n is a integer from 2 to 4, especially wherein n is 3, and $R_7$ and $R_8$ are the same and each is methyl or ethyl, especially wherein $R_7$ and $R_8$ are both methyl.

Also, preferred embodiments of this invention are the compound of formula II and their pharmaceutically acceptable salts wherein:

$R_1$ is lower alkyl, especially ethyl.

$R_2$ is hydrogen.

$R_5$ is hydrogen or methoxy, especially hydrogen.

$R_6$ is a heterocyclic of the formula

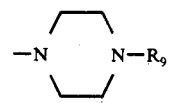

or

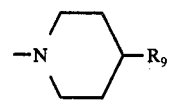

wherein $R_9$ is hydrogen or methyl, especially

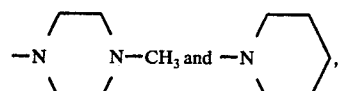

or $R_6$ is a substituted amine of the formula

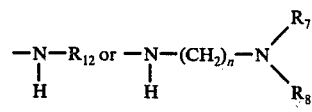

wherein $R_{12}$ is lower alkyl, n is an integer from 2 to 4, especially n is 3, and $R_7$ and $R_8$ are the same and each is methyl or ethyl, especially wherein $R_7$ and $R_8$ are both methyl.

DETAILED DESCRIPTION OF THE INVENTION

The term "lower alkyl" as used throughout this specification is meant to include straight or branched chain hydrocarbon groups having from 1 to 4 carbon atoms, i.e., methyl, ethyl, n-propyl, i-propyl, n-butyl, i-butyl, and t-butyl. Similarly, the term "lower alkoxy" is meant to include such alkyl groups linked to an oxygen atom, i.e. methoxy, ethoxy, t-butoxy, etc. The term "phenyl-lower alkyl" includes such alkyl group linked to a phenyl ring, i.e. benzyl, phenethyl which are preferred.

The term "halogen" represents the four common halogens, Cl, Br, I, and F, preferably Cl and Br, especially Cl.

The compounds of formula I wherein $R_3$ is halogen or lower alkoxy and

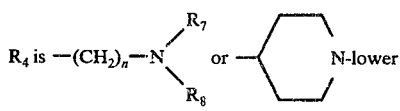

alkyl are prepared by reacting a ketone of the formula

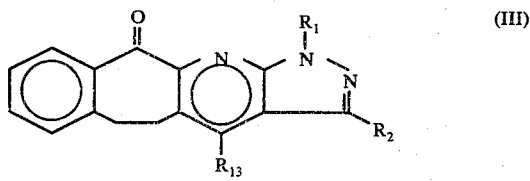

wherein $R_1$ and $R_2$ are as defined above and $R_{13}$ is halogen or lower alkoxy with a Grignard reagent of the formula

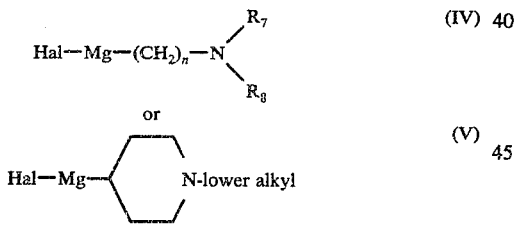

in an inert solvent such as diethyl ether or tetrahydrofuran. The reaction is performed by heating at about reflux temperature for from about 3 to about 8 hours.

The compounds of formula I wherein $R_3$ is hydrogen and $R_4$ is

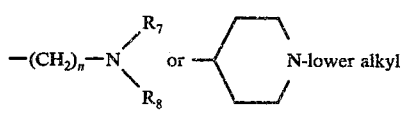

can be prepared by catalytic hydrogenation of the corresponding compound of formula I wherein $R_3$ is halo, preferably Cl, with palladium on charcoal to remove the 4-halo substituent.

The compounds of formula I wherein $R_3$ is halogen or lower alkoxy and $R_4$ is hydrogen are prepared by reduction of the ketone of formula III such as by reaction with an aluminum alkoxide and the corresponding alcohol; i.e. aluminum isopropoxide and isopropanol, or by catalytic hydrogenation of the ketone of formula III such as by treatment with palladium on charcoal at about room temperature for several hours.

The compounds of formula I wherein both $R_3$ and $R_4$ are hydrogen are prepared by the catalytic hydrogenation of the ketone of formula III wherein $R_3$ is halo, preferably Cl, by treatment with palladium on charcoal at an elevated temperature, i.e. from about 50° to about 55° C, for several hours.

Also, the compounds of formula I wherein $R_3$ is lower alkoxy and $R_4$ is hydrogen can be prepared by reducing the ketone of formula III wherein $R_3$ is halo and reacting with an alcohol in a single step, i.e. treatment of the ketone with sodium and an alcohol such as butanol.

Treatment of the compound of formula I wherein $R_3$ is hydrogen or lower alkoxy and $R_4$ is hydrogen with gaseous hydrogen chloride in the presence of calcium chloride yields the intermediate of the formula

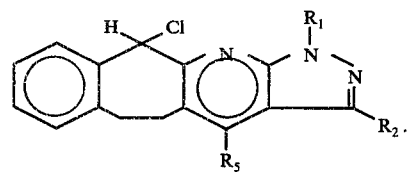

Treatment of the 11-chloro intermediate of formula VI with an amine of the formula

or the formula

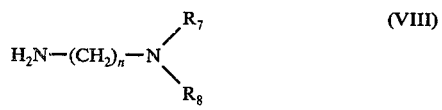

yields the compounds of formula II wherein $R_6$ is

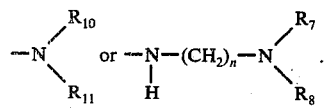

The compounds of formula II wherein $R_5$ is lower alkoxy and $R_6$ is hydrogen,

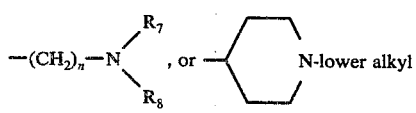

are prepared by catalytic hydrogenation of the corresponding compound of formula I wherein $R_3$ is lower alkoxy and $R_4$ is hydrogen

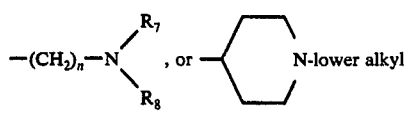

with palladium on charcoal for several hours at about room temperature.

The compounds of formula II wherein $R_5$ is hydrogen and $R_6$ is hydrogen,

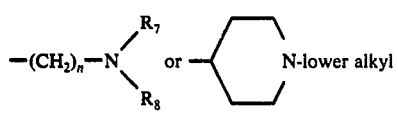

are prepared by catalytic hydrogenation of the corresponding compound of formula I wherein $R_3$ is hydrogen or halogen and $R_4$ is hydrogen,

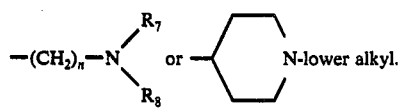

The ketones of formula III are prepared by the following method. A 5-aminopyrazole of the formula

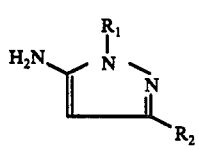    (IX)

[prepared according to the procedure described in Z. F. Chemie 10, 386–388 (1970)] is reacted with a 2-(2-phenylethyl)-acetoacetic acid ester of the formula

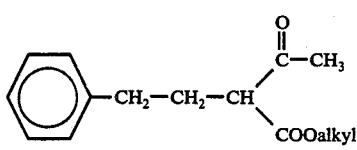    (X)

[prepared according to the procedure described in Annalen der Chemie 395 (1913)], by heating at a temperature of about 140° C. in the presence of polyphosphoric acid producing a compound of the formula

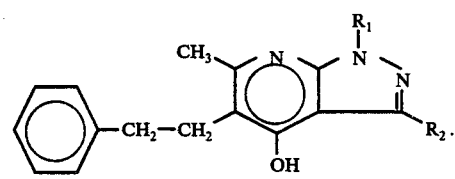    (XI)

This intermediate of formula XI is oxidized with an oxidizing agent such as selenium dioxide in a solvent such as diethyleneglycol dimethyl ether or pyridine at about 140° C to yield a compound of the formula

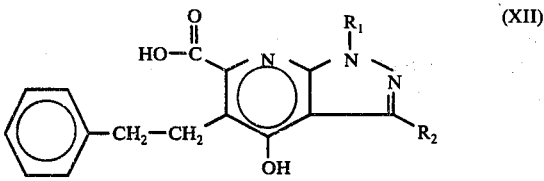    (XII)

which in most cases contain, besides some unreacted compound of formula XI, the aldehyde of the formula

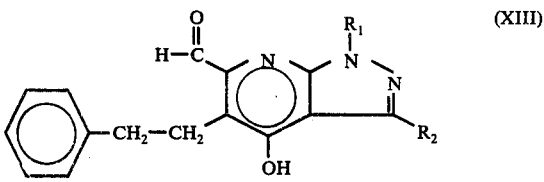    (XIII)

as impurities. Both can be separated by conventional methods. The methyl compound of formula XI can be used again in the oxidation step while the aldehyde of formula XIII is converted to the acid of the formula XII by means of $H_2O_2$ in acetic acid.

The compound of formula XII is then cyclized by heating at a temperature of about 210° C using polyphosphoric acid as the ring closure agent, to produce a product of the formula

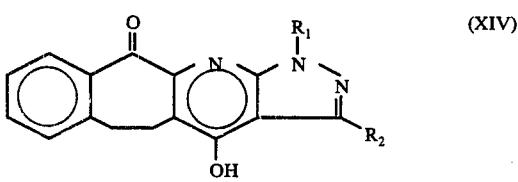    (XIV)

The tetracyclic heterocycle of the formula XIV is treated with an inorganic acid halide such as phosphorus oxychloride, thionyl chloride, thionyl bromide, hydrogen iodide, etc., to yield the ketone of formula III wherein $R_3$ is halo.

The ketone compounds of formula III wherein $R_{13}$ is lower alkoxy can be prepared by alkylating the hydroxy derivative of formula XIV with a lower alkyl halide, preferably a lower alkyl chloride or bromide, in the presence of a base such as potassium carbonate. Alternatively, the ketone of formula III wherein $R_{13}$ is halo can be treated with an appropriate metal alcoholate, i.e., sodium ethoxide, potassium methoxide, etc., to yield the corresponding ketone wherein $R_3$ is lower alkoxy.

The compounds of formulas I and II form salts which are also part of this invention. The salts include acid addition salts, particularly the non-toxic, physiologically acceptable members. These salts are formed by reaction with one or moe equivalents of any of a variety of inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate or aryl- or alkanesulfonates such as benzenesulfonate, methanesulfonate, cyclohexanesulfamate and toluenesulfonate. The acid addition salts frequently provide a convenient means for isolating the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I or II. Other salts can then be formed from the free base by reaction with one or more equivalents of acid containing the desired anion.

The compounds of formulas I and II as well as their pharmaceutically acceptable salts possess antiinflammatory activity. Thus, these compounds can be used for the treatment of inflammation in various mammalian species such as mice, dogs, cats, monkeys, etc., to relieve joint tenderness and stiffness in conditions such as rheumatoid arthritis. Formulation of these compounds can be carried out according to accepted pharmaceutical practice in oral dosage forms such as tablets, capsules, elixers or powders, or in injectable form in a sterile vehicle. The compounds of this invention can be administered in amounts of about 1 to 25 mg. per kilogram per day, preferably 2 to 20 mg. per kilogram per day, in one or more doses.

The compounds of this invention are also psychotropic agents and can be used as ataractic agents for the relief of anxiety and tension states, for example, in mice, cats, rats, dogs and other mammalian species. For this purpose a compound or mixture of compounds of formula I and II, or a non-toxic, physiologically acceptable salt thereof, is administered orally or parenterally in amounts of about 10 to about 100 mg. per kilogram per day, preferably about 5 to about 25 mg. per kilogram per day, in one or more doses. Again, these compounds are formulated according to accepted pharmaceutical practice.

The following examples are illustrative of the invention. All temperatures are in degrees centigrade.

EXAMPLE 1

4-Chloro-1-ethyl-1,5,6,11-tetrahydrobenzo[5,6]cyclohepta[1,2-b]-pyrazolo[4,3-e]pyridin-11-ol (a) 1-Ethyl-6-methyl-5-(2-phenylethyl)-1H-pyrazolo[3,4-b]-pyridin-4-ol 33 g of 5-amino-1-ethylpyrazole (0.3 mol.) in 310 g. of polyphosphoric acid are heated to 80° (bath temperature). While stirring, 70.5 g. of 2-(2-phenylethyl)acetoacetic acid, ethyl ester (0.3 mol.) are added to the mixture. The bath temperature is increased to 100°, the temperature of the solution rising to about 130°. As soon as the reaction temperature begins to drop the bath temperature is elevated to 140° and maintained for 45 minutes. After the mixture has cooled to room temperature, 650 ml. of water are added in portions and stirring is continued until the polyphosphoric acid is dissolved. Then the aqueous phosphoric acid solution is decanted and the undissolved residue is treated with 400 ml. of 5% aqueous ammonia to neutralize the mixture. The mixture is extracted with chloroform and the chloroform extract is washed with water and dried with $Na_2SO_4$. Addition of ether precipitates 37 g. (44%) of 1-ethyl-6-methyl-5-(2-phenylethyl)-1H-pyrazolo[3,4-b]pyridin-4-ol; m.p. 251°-256°. Recrystallizaton from ethanol raises from the m.p. to 258°-260°.

(b) 1-Ethyl-4-hydroxy-5-(2-phenylethyl)-1H-pyrazolo[3,4-b]-pyridine-6-carboxylic acid and 1-ethyl-4-hydroxy-5-(2-phenylethyl)-1H-pyrazolo[3,4-b]pyridine-6-carboxaldehyde, hydrochloride (1:1)

To a suspension of 45 g. of 1-ethyl-6-methyl-5-(2-phenylethyl)-1H-pyrazolo[3,4-b]pyridin-4-ol (0.16 mol.) in 300 ml. of dry pyridine, 44 g. of well pulverized selenium dioxide are added with stirring. The mixture is heated at 130°-140° (bath temperature) for 15 hours. After cooling, the precipitated selenium is filtered off and the filtrate evaporated in vacuo. The remaining oil is stirred with 400 ml. of water and 400 ml. of ether, whereupon 16 g. of the starting material are precipitated. Then the aqueous solution is separated from ether, treated with charcoal and acidified with half concentrated aqueous hydrochloric acid. The precipitated 1-ethyl-4-hydroxy-5-(2-phenylethyl)-1H-pyrazolo-[3,4-b]pyridine-6-carboxylic acid is filtered off, dried in a desiccator over $P_2O_5$ and finally in a drying oven a 100°, yield: 11.7 g. (23.5%); m.p. 250°-251° (ethanol).

The separated ethereal solution is treated with charcoal and dried with $Na_2SO_4$. Addition of ethereal hydrochloric acid precipitates the hydrochloride of 1-ethyl-4-hydroxy-5-(2-phenylethyl)-1H-pyrazolo[3,4-b]-pyridine-6-carboxaldehyde; yield: 9.2 g. (17%); m.p. 255°-257° (dec.) (acetonitrile).

Recrystallization of the carboxaldehyde from ethanol furnishes the acetal, 6-(diethoxymethyl)-1-ethyl-4-hydroxy-5-(2-phenylethyl)-1H-pyrazolo[3,4-b]pyridine hydrochlorie (1:1); m.p. 160°-162° (ethylacetate/abs. ethanol).

(c) 1-Ethyl-4-hydroxy-5-(2-phenylethyl)-1H-pyrazolo[3,4-b]-pyridine-6-carboxylic acid from the carboxaldehyde 16.5 g. of 1-ethyl-4-hydroxy-5-(2-phenylethyl)-1H-pyrazolo[3,4-b]pyridine-6-carboxyaldehyde, hydrochloride (1:1) (0.05 mol.) are dissolved in 150 ml. of boiling glacial acetic acid. To the filtered solution, cooled to about 30°, 10 g. of $H_2O_2$ (35%) (0.1 mol.) are added in two portions and the mixture is allowed to stand for 20 hours at room temperature. The crystalized 1-ethyl-4-hydroxy-5-(2-phenylethyl)-1H-pyrazolo[3,4-b]pyridine-6-carboxylic acid is filtered of, washed with acetic acid and ether, yield: 10.1 g. (65% ); m.p. 250°-251° (ethanol).

(d) 1-Ethyl-5,6-dihydro-4-hydroxybenzo[5,6]cyclohepta[1,2-b]-pyrazolo[4,3-e]pyridin-11(1H)-one 12.4 g. of 1-ethyl-4-hydroxy-5-(2-phenylethyl)-1H-pyrazolo[3,4-b]pyridine-6-carboxylic acid (0.04 mol.) and 150 g. of polyphosphoric acid are heated at 200°-210° (bath temperature) with stirring for 30 minutes. After the mixture has cooled to room temperature 300 ml. of water are added slowly with stirring until the polyphosphoric acid is completely dissolved. The remaining 1-ethyl-5,6-dihydro-4-hydroxybenzo[5,6]cyclohepta[1,2-b]pyrazolo-[4,3-b]pyridin-11-(1H)-one is dissolved in chloroform, the extract is washed twice with water, dried with $Na_2SO_4$ and then evaporated in vacuo, yield: 9 g. (77%); m.p. 190°–192°. Recrystallization from ethanol raises the m.p. to 195°–197°. (e) 4-Chloro-1-ethyl-5,6-dihydrobenzo[5,6]cyclohepta[1,2-b]-pyrazolo[4,3-e]pyridin-11 (1H)-one 41 g. of 1-ethyl-5,6-dihydro-4-hydroxybenzo[5,6-cyclohepta[1,2-b]pyrazolo[4,3-e]pyridin-11(1H)-one (0.14 mol.) and 350 ml. of phosphorus oxychloride are refluxed for 4.5 hours. After cooling, the solution is filtered, the excess phosphorus oxychloride is removed in vacuo and the residue treated with water and extracted with chloroform. The chloroform extract is washed with water, dried with $Na_2SO_4$, treated with charcoal and then evaporated in vacuo to give 38 g. (87%) of 4-chloro-1-ethyl-5,6-dihydrobenzo[5,6]cyclohepta[1,2-b]pyrazolo[4,3-e]pyridin-11(1H)-one; m.p. 156°–159° (ethanol; refrigerator).

(f) 4-Chloro-1-ethyl-1,5,6,11-tetrahydrobenzo[5,6]cyclohepta[1,2-b]pyrazolo[4,3-e]pyridin-11-ol 20.2 g. of 4-chloro-1-ethyl-5,6-dihydrobenzo[5,6]cyclohepta[1,2-b]pyrazolo[4,3-e]pyridin-11(1H)-one (0.065 mol.) and 13 g. of triethylamine (0.13 mol.), dissolved in 400 ml. of ethyl acetate and 75 ml. of absolute ethanol, are catalytically hydrogenated in the presence of 2 g. of palladium on charcoal (10%) at room temperature. In about 6 hours, the theoretical amount of hydrogen is absorbed. The catalyst is then filtered off, the filtrate evaporated in vacuo and the residue extracted with 200 ml. of ether. The ethereal extract is washed with water, dried with $Na_2SO_4$ and the ether removed. The resulting material is recrystallized from petroleum ether (60°–70°) to yield 12.7 g. (62.5%) of 4-chloro-1-ethyl-1,5,6,11-tetrahydro[5,6]cyclohepta[1,2-b]pyrazolo[4,3-e]pyridin-11-ol; m.p. 128°–130°.

EXAMPLE 2

1-Ethyl-1,5,6,11-tetrahydrobenzo[5,6]cyclohepta[1,2-b]pyrazolo[4,3-e]pyridin-11-ol 9.3 g. of 4-chloro-1-ethyl-5,6-dihydrobenzo[5,6]-cyclohepta[1,2-b]pyrazolo[4,3-e]pyridin-11(1H)-one (0.03 mol.) from example 1(e), and 3.6 g. of triethylamine (0.036 mol.) are dissolved in 150 ml. of absolute ethanol and 100 ml. of ethyl acetate. 1 g. of palladium on charcoal (10%) is added and the mixture is hydrogenated at 50°–55° and a hydrogen pressure of 3 atmospheres. When the theoretical amount of hydrogen is absorbed (about 8 hours), the catalyst is filtered off and the filtrate is evaporated to dryness. The residual material is treated with water, filtered off and dried in a desiccator over phosphorous pentaoxide to yield 7.2 g. (86%) of 1-ethyl-1,5,6,11-tetrahydrobenzo[5,6]cyclohepta[1,2-b]-pyrazolo[4,3-e]pyridin-11-ol; m.p. 130°–132° (hexane/cyclohexane (8:2), refrigerator).

EXAMPLE 3

4-Ethoxy-1-ethyl-1,5,6,11-tetrahydrobenzo[5,6]cyclohepta-[1,2-b]pyrazolo[4,3-e]pyridin-11-ol (a) 4-Ethoxy-1-ethyl-5,6-dihydrobenzo[5,6]cyclohepta[1,2-b]-pyrazolo[4,3-e]pyridin-11(1H)-one 6.2 g. of 4-chloro-1-ethyl-5,6-dihydrobenzo[5,6]-cyclohepta[1,2-b]pyrazolo[4,3-e]pyridin-11(1H)-one (0.02 mol.), from example 1(e), are added to a solution of 0.5 g. of sodium (0.022 mol.) in 150 ml. of absolute ethanol. The mixture is heated at 120° (bath temperature) in an autoclave for four hours. After cooling, the crystallized 4-ethoxy-1-ethyl-5,6-dihydrobenzo[5,6]cyclohepta[1,2-b]pyrazolo[4,3-e]pyridin-11-(1H)-one is filtered off and washed with water; yield: 3.5 g. An additional crop of 2.1 g. is obtained by work up of the mother liquor, total yield: 5.6 g. (87.5%); m.p. 150°–152° (ethanol; refrigerator).

(b) 4-Ethoxy-1-ethyl-1,5,6,11-tetrahydrobenzo[5,6]cyclohepta[1,2-b]pyrazolo[4,3-e]pyridin-11-ol Hydrogenation of the 4-ethoxy-1-ethyl-5,6-dihydrobenzo-[5,6]cyclohepta[1,2-b]pyrazolo[4,3-e]pyridin-11(1H)-one from part (a) according to the procedure of example 1(f) yields 4-ethoxy-1-ethyl-1,5,6,11-tetrahydrobenzo[5,6]cyclohepta[1,2-b]pyrazolo[4,3-e]pyridin-11-ol.

EXAMPLES 4–13

Following the procedure of example 1(f) but employing the 4-substituted compound shown in Col. I one obtains the product shown in Col. II.

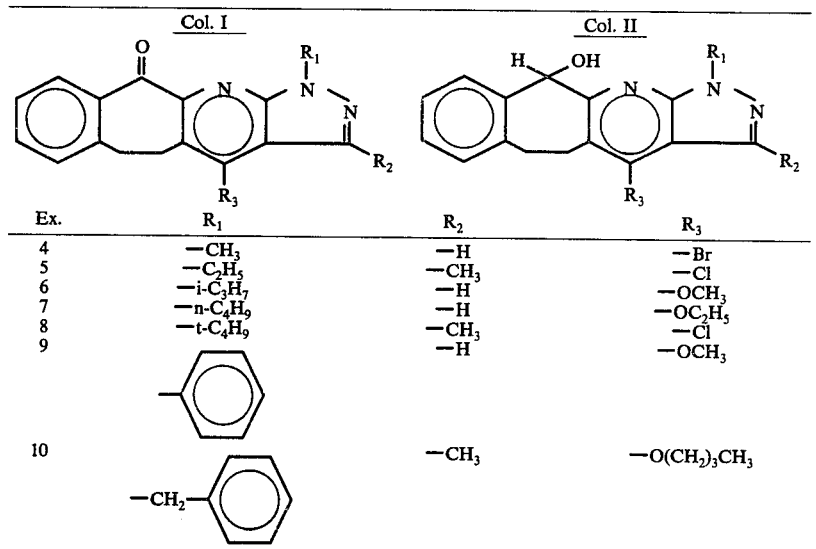

| Ex. | $R_1$ | $R_2$ | $R_3$ |
|---|---|---|---|
| 4 | —$CH_3$ | —H | —Br |
| 5 | —$C_2H_5$ | —$CH_3$ | —Cl |
| 6 | —i-$C_3H_7$ | —H | —$OCH_3$ |
| 7 | —n-$C_4H_9$ | —H | —$OC_2H_5$ |
| 8 | —t-$C_4H_9$ | —$CH_3$ | —Cl |
| 9 | ⟨phenyl⟩ | —H | —$OCH_3$ |
| 10 | —$CH_2$—⟨phenyl⟩ | —$CH_3$ | —$O(CH_2)_3CH_3$ |

-continued

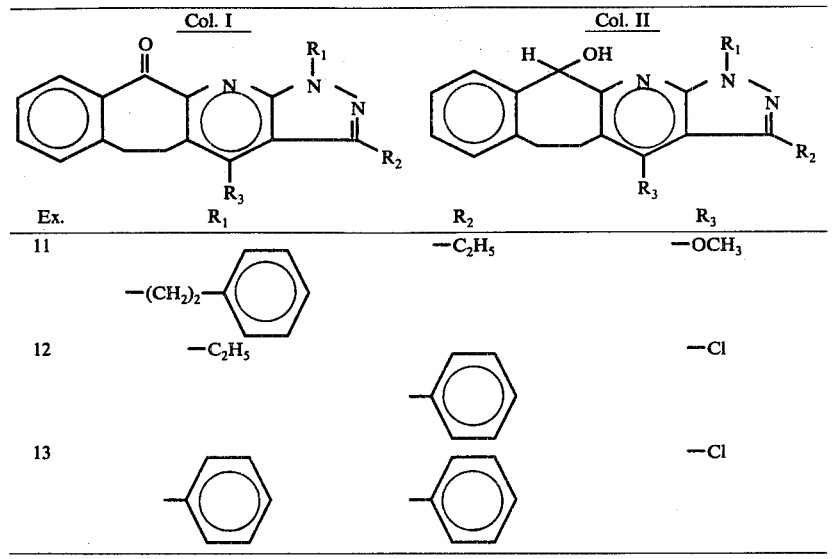

| Ex. | $R_1$ | $R_2$ | $R_3$ |
|---|---|---|---|
| 11 | —(CH$_2$)$_2$—C$_6$H$_5$ | —C$_2$H$_5$ | —OCH$_3$ |
| 12 | —C$_2$H$_5$ | —C$_6$H$_5$ | —Cl |
| 13 | —C$_6$H$_5$—CH$_3$ | —C$_6$H$_5$ | —Cl |

EXAMPLE 14

4-Butoxy-1-ethyl-1,5,6,11-tetrahydrobenzo[5,6]cyclohepta-[1,2-b]pyrazolo[4,3-e]pyridin-11-ol 12.4 g. of 4-chloro-1-ethyl-5,6-dihydrobenzo[5,6]cyclohepta[1,2-b]pyrazolo[4,3-e]pyridin-11(1H)-one (0.04 mol.), from example 1(e), are added to a solution of 2.5 g. of sodium (0.11 mol.) in 130 ml. of butanol. The mixture is heated at 130° (bath temperature) for 6 hours in an autoclave. After cooling, the mixture is evaporated in vacuo and the residue is treated with ether. The undissolved material is filtered off, washed with water, and recrystallized from ethanol to yield 7.1 g. (51%) of 4-butoxy-1-ethyl-1,5,6,11-tetrahydrobenzo[5,6]cyclohepta[1,2-b]pyrazolo[4,3-e]pyridin-11-ol; m.p. 163°–165°.

EXAMPLE 15

4-Chloro-11-[3-dimethylamino)-propyl]-1-ethyl-1,5,6,11-tetrahydrobenzo[5,6]cyclohepta[1,2-b]pyrazolo[4,3-e]pyridin-11-ol, hydrochloride (1:1)

12.3 g. of freshly distilled and absolutely dry 3-(dimethylamino)propyl chloride (0.1 mol.) are added slowly with stirring and gentle heating to 2.4 g. of magnesium turnings in 70 ml. of dry tetrahydrofuran. A crystal of iodine and a few drops of ethyl iodide are employed as initiator. After all of the 3-(dimethylamino)propyl chloride is added, the reaction mixture is refluxed for two to three hours. To this Grignard reagent a solution of 10.8 g. of 4-chloro-1-ethyl-5,6-dihydrobenzo[5,6]cyclohepta[1,2-b]-pyrazolo[4,3-e]pyridin-11(1H)-one (0.035 mole.), from example 1(e), in 70 ml. of dry tetrahydrofuran is added. The mixture is heated under reflux for 5 hours after which the solvent is evaporated and the residue treated with 150 ml. of water and 60 ml. of ammonium chloride solution (20%). The mixture is extracted with ether and the ethereal extract is washed with water and dried with Na$_2$SO$_4$. Then the ethereal solution is allowed to stand over night in a refrigerator to separate unreacted starting material (2.6 g. of oil). The decanted solution is charcoaled, filtered and 8 ml. of ethereal hydrochloric acid (195 g./l.) are added. Stirring is continued for 40 minutes. The precipitated hydrochloride salt is filtered off, washed with ether, and recrystallized from ethyl acetate/ether (1:5) to yield 8.3 g. (55%) of 4-chloro-11-[3-(dimethylamino)propyl]-1-ethyl-1,5,6,11-tetrahydro-[5,6]-cyclohepta[1,2-b]pyrazolo[4,3-e]pyridin-11-ol, hydrochloride (1:1); m.p. 172°–176° (dec.).

EXAMPLE 16

11-[3-Dimethylamino)propyl]-1-ethyl-1,5,6,11-tetrahydro-4-methoxybenzo[5,6]cyclohepta[1,2-b]pyrazolo[4,3-e]pyridin-11-ol, hydrochloride (1:2)

(a) 1-Ethyl-5,6-dihydro-4-methoxybenzo[5,6]cyclohepta[1,2-b]pyrazolo[4,3-e]pyridin-11(1H)-one Sodium methoxide is substituted for the sodium ethoxide in example 3(a) yielding 1-ethyl-5,6-dihydro-4-methoxybenzo[5,6]cyclohepta[1,2-b]pyrazolo[4,3-e]pyridin-11(1H)-one; m.p. 197°–200° (absolute ethanol).

(b) 11-[3-(Dimethylamino)propyl]-1-ethyl-1,5,6,11-tetrahydro-4-methoxybenzo[5,6]cyclohepta[1,2-b]pyrazolo[4,3-e]pyridin-11-ol, hydrochloride (1:2)

A Grignard reagent is prepared from 5 g. of magnesium turnings (0.21 mol.), 150 ml. of dry tetrahydrofuran, and 25.8 g. of 3-(dimethylamino)propyl chloride. To this Grignard reagent a solution of 21.5 g. of 1-ethyl-5,6-dihydro-4-methoxybenzo[5,6]cyclohepta[1,2-b]pyrazolo[4,3-e]pyridin-11(1H)-one (0.07 mol.), from part (a), in 300 ml. of dry tetrahydrofuran is added. Reaction and work-up according to the procedure of example 15 yields, following recrystallization from hexane, 15 g. (54.5%) of 11-[3-(dimethylamino)propyl]-1-ethyl-1,5,6,11-tetrahydro-4-methoxybenzo[5,6]cyclohepta[1,2-b]pyrazolo[4,3-e]-pyridin-11-ol; m.p. 103°–106°.

This material is dissolved in dry ether and treated with ethereal hydrochloric acid to yield 11-[3-(dimethylamino)propyl]-1-ethyl-1,5,6,11-tetrahydro-4- methoxybenzo[5,6]cyclohepta[1,2-b]pyrazolo[4,3-e]pyridin-11-ol, hydrochloride (1:2); m.p. 106°–108°.

EXAMPLE 17

4-Chloro-1-ethyl-1,5,6,11-tetrahydro-11-(1-methyl-4-piperidinyl)-benzo[5,6]cyclohepta[1,2-b]pyrazolo[4,3-e]pyridin-11-ol, hydrochloride (1:2)

A Grignard reagent is prepared from 7.2 g. of magnesium turnings (0.3 mol.), 230 ml. of dry tetrahydrofuran and 40 g. of 4-chloro-1-methyl-piperidine (0.3 mol.). To this Grignard solution 31 g. of 4-chloro-1-ethyl-5,6-dihydrobenzo[5,6]cyclohepta[1,2-b]pyrazolo[4,3-e]pyridin-11(1H)-one (0.1 mol.), from example 1(e), dissolved in 230 ml. of dry tetrahydrofuran is added. Reaction and work-up according to the procedure of example 15 yields 4-chloro-1-ethyl-1,5,6,11-tetrahydro-11-(1-methyl-4-piperidinyl)benzo[5,6]cyclohepta[1,2-b]pyrazolo[4,3-e]pyridin-11-ol; m.p. 130°–132° (hexane, refrigerator).

This material is dissolved in dry ether and treated with ethereal hydrochloric acid to yield 21 g. of 4-chloro1-ethyl-1,5,6,11-tetrahydro-11-(1-methyl-4-piperidinyl)benzo[5,6-cyclohepta[1,2-b]pyrazolo[4,3-e]pyridin-11-ol, hydrochloride (1:2); m.p. 210°–212° (dec.).

EXAMPLE 18

1-Ethyl-1,5,6,11-tetrahydro-4-methoxy-11-(1-methyl-4-piperidinyl)-benzo[5,6]cyclohepta[1,2-b]pyrazolo[4,3-e]pyridin-11-ol, hydrochloride (1:1)

Following the procedure of example 17, but substituting 1-ethyl-5,6-dihydro-4-methoxybenzo[5,6]cyclohepta[1,2-b]pyrazolo[4,3-e]pyridin-11(1H)-one from example 16(a) for the 4-chloro compound one obtains 1-ethyl-1,5,6,11-tetrahydro-4-methoxy-11-(1-methyl-4-piperidinyl)benzo[5,6]cyclohepta[1,2-b]pyrazolo[4,3-e]pyridin-11ol; m.p. 90°–93° and its hydrochloride (1:1); m.p. 217°–220° (dec.) (ethylacetate).

EXAMPLES 19–42

Following the procedure of example 15 but employing the compound of Col. I and the Grignard reagent of Col. II, one obtains the final products shown in Col. III.

| Ex. | Col. I $R_1$ | $R_2$ | $R_3$ | Col. II Cl—Mg—X | Col. III X |
|---|---|---|---|---|---|
| 19 | —H | —H | —Cl | | —(CH$_2$)$_4$—N(CH$_3$)$_2$ |
| 20 | —CH$_3$ | —CH$_3$ | —Br | | —(CH$_2$)$_5$—N(C$_2$H$_5$)$_2$ |
| 21 | —C$_2$H$_5$ | —H | —Cl | | —(CH$_2$)$_6$—N(CH$_3$)$_2$ |
| 22 | —C$_2$H$_5$ | —CH$_3$ | —Br | | —(CH$_2$)$_2$N〈piperidinyl〉—CH$_3$ |
| 23 | —C$_2$H$_5$ | —n-C$_3$H$_7$ | —Cl | | —(CH$_2$)$_3$N〈pyrrolidinyl〉 |
| 24 | —n-C$_3$H$_7$ | —H | —Br | | —(CH$_2$)$_3$N(CH$_3$)(C$_2$H$_5$) |
| 25 | —t-C$_4$H$_9$ | —H | —Cl | | —(CH$_2$)$_4$N(C$_2$H$_5$)(CH$_3$) |
| 26 | —C$_6$H$_5$ | —H | —Cl | | —(CH$_2$)$_3$—N(CH$_3$)$_2$ |
| 27 | —CH$_2$—C$_6$H$_5$ | —CH$_3$ | —Br | | 〈piperidinyl〉N—C$_2$H$_5$ |
| 28 | —(CH$_2$)$_2$—C$_6$H$_5$ | —H | —Cl | | 〈piperidinyl〉N—i-C$_3$H$_7$ |
| 29 | —C$_2$H$_5$ | —C$_6$H$_5$ | —Cl | | 〈piperidinyl〉N—CH$_3$ |

-continued

| | Col. I | | Col. II | Col. III | |
|---|---|---|---|---|---|
| Ex. | $R_1$ | $R_2$ | $R_3$ | X | |
| 30 | —H | ⟨phenyl⟩ | —OCH$_3$ | —(CH$_2$)$_2$—N(C$_2$H$_5$)$_2$ | |
| 31 | —C$_2$H$_5$ | —CH$_3$ | —OC$_2$H$_5$ | —(CH$_2$)$_3$—N(CH$_3$)$_2$ | |
| 32 | —i-C$_3$H$_7$ | —H | —O(CH$_2$)$_2$CH$_3$ | —(CH$_2$)$_6$—N⟨piperazinyl⟩N—CH$_3$ | |
| 33 | —C$_2$H$_5$ | —C$_2$H$_5$ | —OCH$_3$ | —(CH$_2$)$_3$N(CH$_3$)(C$_2$H$_5$) | |
| 34 | —CH$_2$-⟨phenyl⟩ | —H | —OC$_2$H$_5$ | —(CH$_2$)$_3$—N(C$_2$H$_5$)$_2$ | |
| 35 | —C$_2$H$_5$ | —H | —OCH$_3$ | —(CH$_2$)$_4$—N⟨2-methylpyrrolidinyl⟩ | |
| 36 | —C$_2$H$_5$ | —CH$_3$ | —OCH$_3$ | —(CH$_2$)$_5$—N(CH$_3$)(C$_2$H$_5$) | |
| 37 | —C$_2$H$_5$ | —H | —OCH$_3$ | ⟨1-ethyl-4-piperidyl⟩ | |
| 38 | —CH$_3$ | —CH$_3$ | —OC$_2$H$_5$ | ⟨1-butyl-4-piperidyl⟩ | |
| 39 | —C$_2$H$_5$ | ⟨phenyl⟩ | —OCH$_3$ | ⟨1-methyl-4-piperidyl⟩ | |
| 40 | —C$_2$H$_5$ | —H | —OCH$_3$ | —(CH$_2$)$_3$—N⟨piperazinyl⟩N—C$_2$H$_5$ | |
| 41 | —C$_2$H$_5$ | —H | —OC$_2$H$_5$ | —(CH$_2$)$_4$—N⟨piperazinyl⟩N—H | |
| 42 | —C$_2$H$_5$ | —H | —OCH$_3$ | —(CH$_2$)$_3$—N⟨4-methylpiperidyl⟩CH$_3$ | |

EXAMPLE 43

11-[3-Dimethylamino)propyl]-1-ethyl-1,5,6,11-tetrahydrobenzo-[5,6]cyclohepta[1,2-b]pyrazolo[4,3-e]pyridin-11-ol, hydrochloride (1:2), hydrate (1:1)

8 g. of triethylamine and 1 g. of palladium on charcoal (10%) are added to a solution of 8.6 g. of 4-chloro-11-[3-(dimethylamino)propyl]-1-ethyl-1,5,6,11-tetrahydrobenzo[5,6]cyclohepta[1,2-b]pyrazolo[4,3-e]pyridin-11-ol, hydrochloride (1:1) (0.02 mol.), from example 15, in 200 ml. of absolute ethanol. The mixture is hydrogenated at 45°–50° for 8 hours applying a hydrogen pressure of 2.5-3 atmospheres. The catalyst is then filtered off, the alcohol is removed by distillation and the resulting oil is extracted with ether. The ethereal extract is washed with 100 ml. of water, treated with charcoal, and dried (Na₂SO₄). A solution of 4.5 ml. of ethereal hydrochloric acid (195 g./l.) are added to the residue. The resulting precipitate is filtered off, washed with ether, and dried to yield 7.1 g. (78%) of 11-[3-(dimethylamino)-propyl]-1-ethyl-1,5,6,11-tetrahydrobenzo[5,6]cyclohepta[1,2-b]-pyrazolo[4,3-e]pyridin-11-ol, hydrochloride (1:2); m.p. 102°–104° (dec.), (ethylacetate/ether (1:4)).

Similarly, the 4-halo products shown in Col. III of examples 19 to 29 can be hydrogenated according to the above procedure to yield the corresponding compounds wherein $R_3$ is hydrogen.

EXAMPLE 44

N-Butyl-1-ethyl-1,5,6,11-tetrahydrobenzo[5,6]cyclohepta[1,2-b]-pyrazolo[4,3-e]pyridin-11-amine; hydrochloride (1:1)

(a) 11-Chloro-1-ethyl-1,5,6,11-tetrahydrobenzo[5,6]cyclohepta[1,2-b]pyrazolo[4,3-e]pyridine 6 g. of pulverized CaCl₂ are added with stirring to a solution of 11 g. of 1-ethyl-1,5,6,11-tetrahydrobenzo[5,6]cyclohepta[1,2-b]pyrazolo[4,3-e]pyridin-11-ol (0.04 mol.), from example 2, in 175 ml. of dry benzene. The suspension is saturated for 15 hours with anhydrous hydrogen chloride at room temperature. After standing overnight, the mixture is filtered and the benzene is evaporated in vacuo. The residue is extracted with ether, treated with charcoal, and refrigerated to crystallize 8.3 g. of 11-chloro-1-ethyl-1,5,6,11-tetrahydrobenzo[5,6]cyclohepta[1,2-b]pyrazolo[4,3-e]-pyridine; m.p. 107°–110° (ether).

(b) N-butyl-1-ethyl-1,5,6,11-tetrahydrobenzo[5,6]cyclohepta[1,2-b]pyrazolo[4,3-e]pyridin-11-amine, hydrochloride (1:1)

11.8 g. of 11-chloro-1-ethyl-1,5,6,11-tetrahydrobenzo[5,6]cyclohepta[1,2-b]pyrazolo[4,3-e]pyridine (0.04 mol.), from part (a), and 75 ml. of butylamine are refluxed for 5.5 hours. After evaporation of excessive butylamine, the residue is shaken with 100 ml. of water and 100 ml. of ether. The separated ethereal solution is washed twice with 50 ml. of water, treated with charcoal, dried with Na₂SO₄ and then evaporated to yield 8.7 g. of an oil. This material is dissolved in 125 ml. of ethylacetate and 5 ml. of ethereal hydrochloric acid (195 g./l.) are added to precipitate 8.4 g. of N-butyl-1-ethyl-1,5,6,11-tetrahydrobenzo[5,6]cyclohepta[1,2-b]pyrazolo[4,3-e]pyridin-11-amine, hydrochloride (1:1); m.p. 231°–233° (dec.).

EXAMPLE 45

N-[3-(Dimethylamino)propyl]-1-ethyl-1,5,6,11-tetrahydrobenzo[5,6]-cyclohepta[1,2-b]pyrazolo[4,3-e]pyridin-11-amine, hydrochloride (1:2), hydrate (1:2)

11.8 g. of 11-chloro-1-ethyl-1,5,6,11-tetrahydrobenzo[5,6]cyclohepta[1,2-b]pyrazolo[4,3-e]pyridine (0.04 mol.), from example 44(a), and 75 ml. of 3-(dimethylamino)propylamine are heated at 120°–125° (bath temperature) for 5.5 hours. Following the procedure of example 44(b), 11 g. (76%) of oily N-[3-(dimethylamino)propyl]-1-ethyl-1,5,6,11-tetrahydrobenzo[5,6]-cyclohepta-[1,2-b]pyrazolo[4,3-e]pyridin-11-amine are obtained. Treatment with ethereal hydrochloric acid yields N-[3-(dimethylamino)propyl]-1-ethyl-1,5,6,11-tetrahydrobenzo[5,6]cyclohepta[1,2-b]pyrazolo[4,3-e]pyridin-11-amine, hydrochloride (1:2), hydrate (1:2); m.p. 125° (dec.).

EXAMPLE 46

1-Ethyl-1,5,6,11-tetrahydro-11-(1-piperidinyl)benzo[5,6]-cyclohepta[1,2-b]pyrazolo[4,3-e]pyridine, hydrochloride (1:1)

Following the procedure of example 45 but substituting piperidine for the 3-(dimethylamino)propylamine, oily 1-ethyl-1,5,6,11-tetrahydro-11-(1-piperidinyl)benzo[5,6]cyclohepta[1,2-b]pyrazolo[4,3-e]pyridine is obtained. Treatment with ethereal hydrochloric acid yields 1-ethyl-1,5,6,11-tetrahydro-11-(1-piperidinyl)-benzo[5,6]cyclohepta[1,2-b]pyrazolo[4,3-e]-pyridine, hydrochloride (1:1); m.p. 116° (dec.).

EXAMPLE 47

1-Ethyl-1,5,6,11-tetrahydro-11-(4-methyl-1-piperazinyl(benzo-[5,6]cyclohepta[1,2-b]pyrazolo[4,3-e]pyridine, hydrochloride (1:2)

7.4 g. of 11-chloro-1-ethyl-1,5,6,11-tetrahydrobenzo[5,6]cyclohepta[1,2-b]pyrazolo[4,3-e]pyridine (0.025 mol.), from example 44(a), and 20 ml. of N-methylpiperazine in 60 ml. of benzene are refluxed for 5.5 hours. Following the procedure of example 44(b) yields 8.1 g. of 1-ethyl-1,5,6,11-tetrahydro-11-(4-methyl-1-piperazinyl)benzo[5,6]cyclohepta[1,2-b]pyrazolo[4,3-e]pyridine, hydrochloride (1:2); m.p. 214°–216° (dec.). (ethylacetate).

EXAMPLES 48–69

Following the procedure of example 44 but employing the compounds shown in Col. I and Col. II, one obtains the product shown in Col. III.

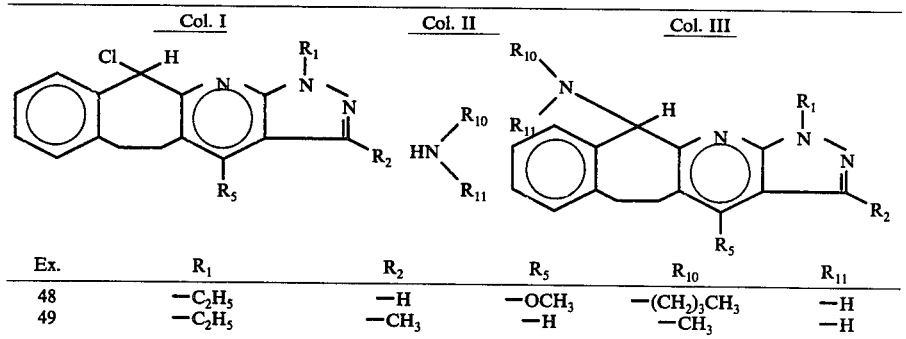

| Ex. | $R_1$ | $R_2$ | $R_5$ | $R_{10}$ | $R_{11}$ |
|---|---|---|---|---|---|
| 48 | —C₂H₅ | —H | —OCH₃ | —(CH₂)₃CH₃ | —H |
| 49 | —C₂H₅ | —CH₃ | —H | —CH₃ | —H |

-continued

| | Col. I | Col. II | | Col. III | |
|---|---|---|---|---|---|
| Ex. | $R_1$ | $R_2$ | $R_5$ | $R_{10}$ | $R_{11}$ |
| 50 | —H | —$CH_3$ | —$OC_2H_5$ | —$CH_3$ | —$CH_3$ |
| 51 | —t-$C_4H_9$ | —H | —H | —$(CH_2)_2CH_3$ | —H |
| 52 | —$C_2H_5$ | —$C_2H_5$ | —$OCH_3$ | —$C_2H_5$ | —H |
| 53 | —$C_2H_5$ | —phenyl | —H | —$C_2H_5$ | —$C_2H_5$ |
| 54 | —$CH_2$-phenyl | —H | —H | —$CH_3$ | —H |
| 55 | -phenyl | —H | —$OCH_3$ | —$CH_3$ | —$CH_3$ |
| 56 | —$C_2H_5$ | —H | —$OCH_3$ | \multicolumn{2}{c}{—N(4-methylpiperidine)} |
| 57 | —$CH_3$ | —$C_2H_5$ | —H | \multicolumn{2}{c}{—N(piperidine)} |
| 58 | —$C_2H_5$ | —$CH_3$ | —$OCH_3$ | \multicolumn{2}{c}{—N(3-methylpiperidine)} |
| 59 | —$CH_2$-phenyl | —H | —H | \multicolumn{2}{c}{—N(4-ethylpiperidine)} |
| 60 | —$C_2H_5$ | -phenyl | —H | \multicolumn{2}{c}{—N(4-ethylpiperidine)} |
| 61 | —$C_2H_5$ | —$CH_3$ | —$OCH_3$ | \multicolumn{2}{c}{—N(pyrrolidine)} |
| 62 | —n-$C_3H_7$ | —H | —H | \multicolumn{2}{c}{—N(pyrrolidine)} |
| 63 | —$C_2H_5$ | —H | —$OCH_3$ | \multicolumn{2}{c}{—N(3-methylpyrrolidine)} |
| 64 | —$C_2H_5$ | —H | —H | \multicolumn{2}{c}{—N(3-methylpyrrolidine)} |

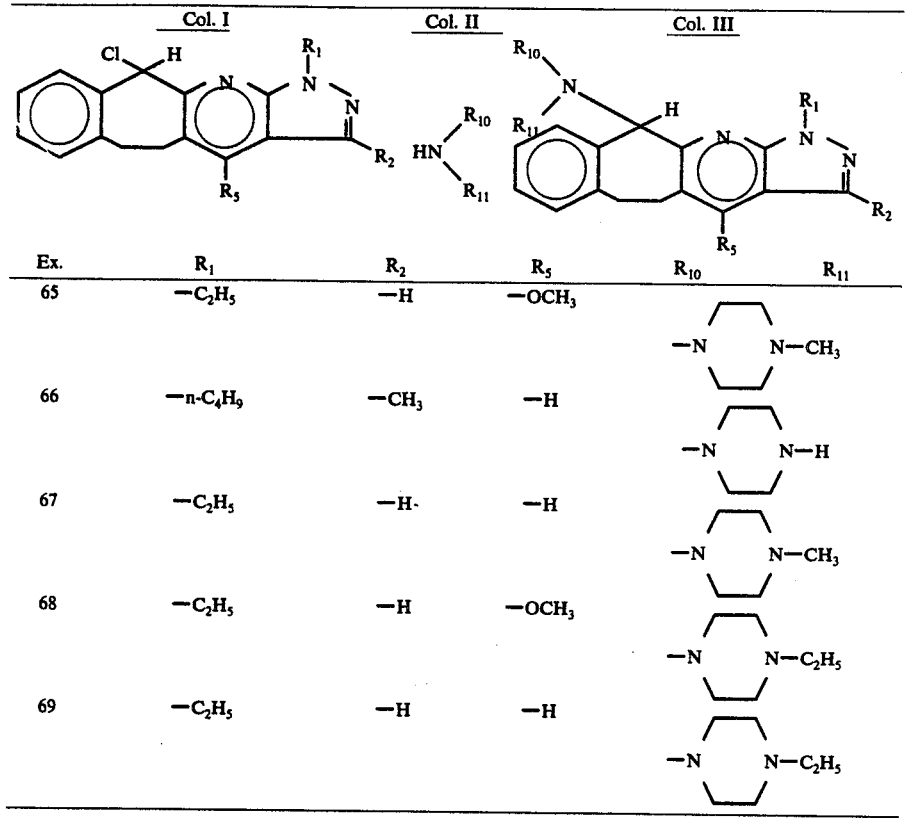

| Ex. | $R_1$ | $R_2$ | $R_5$ | $R_{10}$ | $R_{11}$ |
|---|---|---|---|---|---|
| 65 | $-C_2H_5$ | $-H$ | $-OCH_3$ | | $-N\underset{\phantom{x}}{\bigcirc}N-CH_3$ |
| 66 | $-n-C_4H_9$ | $-CH_3$ | $-H$ | | $-N\underset{\phantom{x}}{\bigcirc}N-H$ |
| 67 | $-C_2H_5$ | $-H$ | $-H$ | | $-N\underset{\phantom{x}}{\bigcirc}N-CH_3$ |
| 68 | $-C_2H_5$ | $-H$ | $-OCH_3$ | | $-N\underset{\phantom{x}}{\bigcirc}N-C_2H_5$ |
| 69 | $-C_2H_5$ | $-H$ | $-H$ | | $-N\underset{\phantom{x}}{\bigcirc}N-C_2H_5$ |

EXAMPLES 70–91

Following the procedure of example 45 but employing the compounds shown in Col. I and Col. II, one obtains the product shown in Col. III.

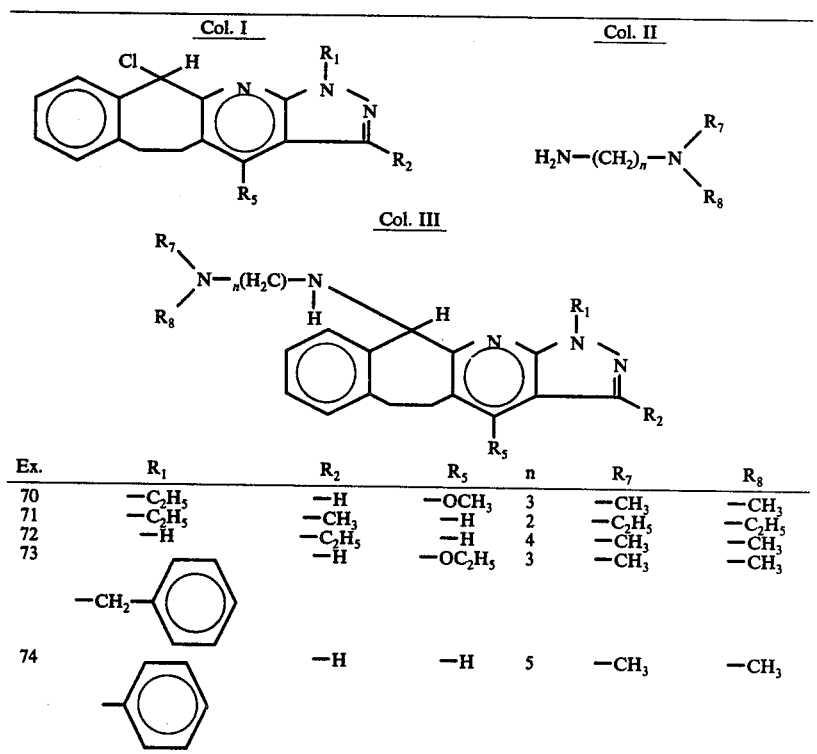

| Ex. | $R_1$ | $R_2$ | $R_5$ | n | $R_7$ | $R_8$ |
|---|---|---|---|---|---|---|
| 70 | $-C_2H_5$ | $-H$ | $-OCH_3$ | 3 | $-CH_3$ | $-CH_3$ |
| 71 | $-C_2H_5$ | $-CH_3$ | $-H$ | 2 | $-C_2H_5$ | $-C_2H_5$ |
| 72 | $-H$ | $-C_2H_5$ | $-H$ | 4 | $-CH_3$ | $-CH_3$ |
| 73 | $-CH_2-\phenyl$ | $-H$ | $-OC_2H_5$ | 3 | $-CH_3$ | $-CH_3$ |
| 74 | $-\phenyl-CH_3$ | $-H$ | $-H$ | 5 | $-CH_3$ | $-CH_3$ |

-continued

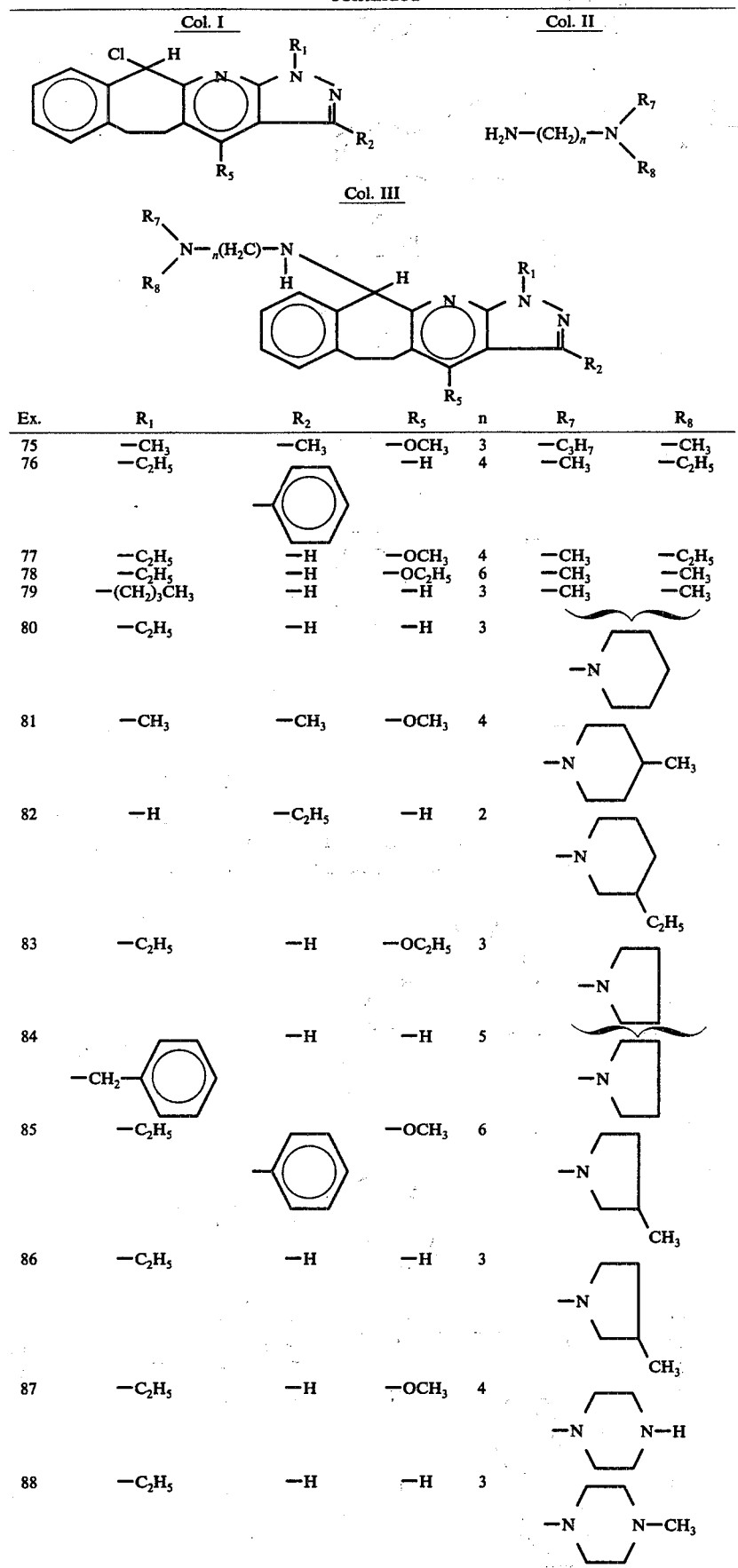

| Ex. | R₁ | R₂ | R₅ | n | R₇ | R₈ |
|---|---|---|---|---|---|---|
| 75 | —CH₃ | —CH₃ | —OCH₃ | 3 | —C₃H₇ | —CH₃ |
| 76 | —C₂H₅ | —C₆H₄CH₃ (p-tolyl) | —H | 4 | —CH₃ | —C₂H₅ |
| 77 | —C₂H₅ | —H | —OCH₃ | 4 | —CH₃ | —C₂H₅ |
| 78 | —C₂H₅ | —H | —OC₂H₅ | 6 | —CH₃ | —CH₃ |
| 79 | —(CH₂)₃CH₃ | —H | —H | 3 | —CH₃ | —CH₃ |
| 80 | —C₂H₅ | —H | —H | 3 | piperidino | |
| 81 | —CH₃ | —CH₃ | —OCH₃ | 4 | 4-methylpiperidino | |
| 82 | —H | —C₂H₅ | —H | 2 | 3-ethylpiperidino | |
| 83 | —C₂H₅ | —H | —OC₂H₅ | 3 | pyrrolidino | |
| 84 | —CH₂C₆H₅ | —H | —H | 5 | pyrrolidino | |
| 85 | —C₂H₅ | —C₆H₅ | —OCH₃ | 6 | 3-methylpyrrolidino | |
| 86 | —C₂H₅ | —H | —H | 3 | 3-methylpyrrolidino | |
| 87 | —C₂H₅ | —H | —OCH₃ | 4 | piperazino (N—H) | |
| 88 | —C₂H₅ | —H | —H | 3 | 4-methylpiperazino | |

-continued

| | Col. I | Col. II |
|---|---|---|

Col. III

| Ex. | $R_1$ | $R_2$ | $R_5$ | n | $R_7$ | $R_8$ |
|---|---|---|---|---|---|---|
| 89 | $-C_2H_5$ | $-H$ | $-OCH_3$ | 3 | | $-N\diagdown\diagup N-C_2H_5$ |
| 90 | $-CH_3$ | $-H$ | $-H$ | 4 | | $-N\diagdown\diagup N-C_2H_5$ |
| 91 | $-C_2H_5$ | $-CH_3$ | $-H$ | 3 | | $-N\diagdown\diagup N-CH_3$ |

EXAMPLES 92–105

Halogenation of the compound of Col. I by treatment with $CaCl_2$ according to the procedure of Example 44(a) followed by hydrogenation by treatment with palladium on charcoal (10%) at about 60° while applying a hydrogen pressure of about 3 atmospheres yields the products shown in Col. II.

| | Col. I | Col. II |
|---|---|---|

| Ex. | $R_1$ | $R_2$ | $R_3$ | $R_4$ | $R_5$ | $R_6$ |
|---|---|---|---|---|---|---|
| 92 | $-C_2H_5$ | $-H$ | $-Cl$ | $-H$ | $-H$ | $-H$ |
| 93 | $-C_2H_5$ | $-H$ | $-OCH_3$ | $-H$ | $-OCH_3$ | $-H$ |
| 94 | $-H$ | $-CH_3$ | $-H$ | $-H$ | $-H$ | $-H$ |
| 95 | $-CH_2-C_6H_5$ | $-C_2H_5$ | $-Cl$ | $-H$ | $-H$ | $-H$ |
| 96 | $-C_6H_5$ | $-H$ | $-Cl$ | $-(CH_2)_3-N(CH_3)_2$ | $-H$ | $-(CH_2)_3N(CH_3)_2$ |
| 97 | $-i-C_3H_7$ | $-CH_3$ | $-OCH_3$ | $-(CH_2)_4-N\diagdown\diagup$ (piperidine) | $-OCH_3$ | $-(CH_2)_4-N\diagdown\diagup$ (piperidine) |
| 98 | $-H$ | $-C_6H_5$ | $-H$ | $-(CH_2)_5-N\diagdown\diagup-CH_3$ | $-H$ | $-(CH_2)_5N\diagdown\diagup-CH_3$ |

-continued

| | Col. I | | | | Col. II | |
|---|---|---|---|---|---|---|
| Ex. | $R_1$ | $R_2$ | $R_3$ | $R_4$ | $R_5$ | $R_6$ |
| 99 | $-C_2H_5$ | $-H$ | $-OCH_3$ | $-(CH_2)_3N\langle\text{3-methylpyrrolidinyl}\rangle$ | $-OCH_3$ | $-(CH_2)_3N\langle\text{3-methylpyrrolidinyl}\rangle$ |
| 100 | $-C_2H_5$ | $-H$ | $-Cl$ | $-(CH_2)_4N\langle\text{N-methylpiperazinyl}\rangle$ | $-H$ | $-(CH_2)_4N\langle\text{N-methylpiperazinyl}\rangle$ |
| 101 | $-C_2H_5$ | $-H$ | $-H$ | $-(CH_2)_3N\langle\text{N-methylpiperazinyl}\rangle$ | $-H$ | $-(CH_2)_3N\langle\text{N-methylpiperazinyl}\rangle$ |
| 102 | $-CH_3$ | $-H$ | $-OCH_3$ | piperidinyl-$N-CH_3$ | $-OCH_3$ | piperidinyl-$N-CH_3$ |
| 103 | $-C_2H_5$ | $-CH_3$ | $-H$ | piperidinyl-$N-C_2H_5$ | $-H$ | piperidinyl-$N-C_2H_5$ |
| 104 | $-CH_2C_6H_5$ | $-H$ | $-Cl$ | piperidinyl-$N-C_3H_7$ | $-H$ | piperidinyl-$N-C_3H_7$ |
| 105 | $-C_2H_5$ | $-C_2H_5$ | $-OCH_3$ | piperidinyl-$N-CH_3$ | $-OCH_3$ | piperidinyl-$N-CH_3$ |

What is claimed is:

1. A compound of the formula:

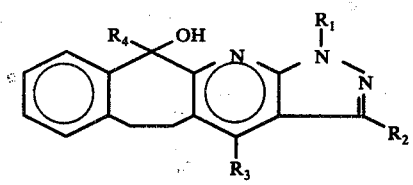

wherein $R_1$ is lower alkyl, phenyl, or phenyl-lower alkyl; $R_2$ is hydrogen, lower alkyl, or phenyl; $R_3$ is hydrogen, halogen, or lower alkoxy; $R_4$ is

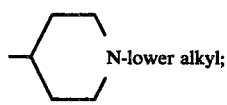

and a pharmaceutically acceptable salt thereof.

2. The compound of claim 1 wherein $R_1$ is lower alkyl of 1 to 4 carbons; $R_2$ is hydrogen; $R_3$ is hydrogen, Cl, Br, or lower alkoxy of 1 to 4 carbons; $R_4$ is

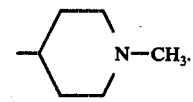

3. The compound of the claim 2 wherein $R_1$ is ethyl; $R_3$ is hydrogen, Cl, or methoxy; and $R_4$ is

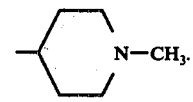

4. The compound of claim 3 wherein $R_3$ is Cl and $R_4$ is

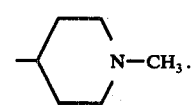

5. The compound of claim 3 wherein $R_3$ is methoxy and $R_4$ is

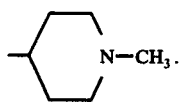
6. A salt of the compound of claim 4, 4-chloro-1-ethyl-1,5,6,11-tetrahydro-11-(1-methyl-4-piperidinyl)-benzo[5,6]-cyclohepta[1,2-b]-pyrazolo[4,3-e]pyridin-11-ol, hydrochloride(1:2).
7. A salt of the compound of claim 5, 1-ethyl-1,5,6,11-tetrahydro-4-methoxy-11-(1-methyl-4-piperidinyl)-benzo[5,6]cyclhepta-[1,2-b]pyrazolo[4,3-e]pyridin-11-ol, hydrochloride(1:1).
* * * * *

UNITED STATES PATENT AND TRADEMARK OFFICE
CERTIFICATE OF CORRECTION

PATENT NO. : 4,111,940
DATED : September 5, 1978
INVENTOR(S) : Hans Hoehn et al.

It is certified that error appears in the above-identified patent and that said Letters Patent are hereby corrected as shown below:

Col. 6, line 60, "or moe" should read -- or more --.
Col. 8, line 51, "filtered of" should read -- filtered off --.

Signed and Sealed this

Fifteenth Day of May 1979

[SEAL]

Attest:

RUTH C. MASON
*Attesting Officer*

DONALD W. BANNER
*Commissioner of Patents and Trademarks*